(12) United States Patent
Gunji

(10) Patent No.: US 8,913,240 B2
(45) Date of Patent: Dec. 16, 2014

(54) FLUORESCENCE SPECTROPHOTOMETER

(75) Inventor: Masahide Gunji, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 0 days.

(21) Appl. No.: 13/980,354

(22) PCT Filed: Sep. 30, 2011

(86) PCT No.: PCT/JP2011/072504
§ 371 (c)(1),
(2), (4) Date: Jul. 18, 2013

(87) PCT Pub. No.: WO2013/046418
PCT Pub. Date: Apr. 4, 2013

(65) Prior Publication Data
US 2014/0190243 A1    Jul. 10, 2014

(51) Int. Cl.
*G01J 3/30* (2006.01)
*G01J 3/44* (2006.01)
*G01N 30/74* (2006.01)
*G01J 3/06* (2006.01)
*G01J 3/18* (2006.01)
*G01J 3/42* (2006.01)
*G01N 21/64* (2006.01)

(52) U.S. Cl.
CPC ............... *G01J 3/4406* (2013.01); *G01N 30/74* (2013.01); *G01J 3/06* (2013.01); *G01J 3/18* (2013.01); *G01J 3/42* (2013.01); *G01N 21/64* (2013.01); *G01N 2021/6417* (2013.01); *G01N 2021/6419* (2013.01); *G01N 2021/6421* (2013.01)
USPC ........................................................ 356/317

(58) Field of Classification Search
USPC ................................................ 356/300–334
See application file for complete search history.

(56) References Cited

U.S. PATENT DOCUMENTS 7,352,459 B2 *   4/2008   Gould et al. .................. 356/318

FOREIGN PATENT DOCUMENTS

| JP | 01-212323 | 8/1989 |
| JP | 03-144347 U | 6/1991 |
| JP | H06109542 A | 4/1994 |
| JP | 2000-346805 A | 12/2000 |
| JP | 3132835 U | 6/2007 |
| JP | 2008-286562 A | 11/2008 |

OTHER PUBLICATIONS

Japanese Office Action mailed Sep. 17, 2013 for corresponding Japanese Patent App. No. 2010-142452.
English translation of "Reason for Rejection" for Japanese Office Action mailed Sep. 17, 2013 for corresponding Japanese Patent App. No. 2010-142452.
International Search Report mailed Jan. 10, 2012 for International Application No. PCT/JP2011/072504 (3 pages).

* cited by examiner

*Primary Examiner* — Tarifur Chowdhury
*Assistant Examiner* — Abdullahi Nur
(74) *Attorney, Agent, or Firm* — Bingham McCutchen LLP

(57) ABSTRACT

A fluorescence spectrophotometer according to the present invention includes: a light source 1; a sample cell 3; an excitation-side light-dispersing system 2 for dispersing a light from the light source 1 and for casting a desired wavelength of light into the sample cell 3; an emission-side light-dispersing system 4 for dispersing a light emitted from the sample cell 3, the emission-side light-dispersing system 4 being located off an optical path of a transmitted light exiting from the sample cell 3 after being cast from the excitation-side light-dispersing system 2 into the sample cell 3; and a photodetector 5 capable of detecting, among the light from the emission-side light-dispersing system 4, an emission light having the same wavelength as the light cast from the excitation-side light-dispersing system 2 into the sample cell 3.

3 Claims, 3 Drawing Sheets

FLUORESCENCE SPECTROPHOTOMETER

TECHNICAL FIELD

The present invention relates to a fluorescence spectrophotometer in which a specific wavelength of light is cast onto a sample as excitation light and the amount of light emitted from the excited sample is measured.

BACKGROUND ART

A fluorescence spectrophotometer is an apparatus for analyzing a sample by casting an excitation light onto the sample to bring it into an excited state and for measuring the intensity of fluorescence which is emitted when the sample returns from the excited state to the ground state.

A common type of fluorescence spectrophotometer is hereinafter described by means of FIG. 1 (Patent Document 1). The fluorescence spectrophotometer has a light source 1, an excitation-side light-dispersing device 2, a sample cell 3, an emission-side light-dispersing device 4 and a detector 5. The light produced by the light source 1 is dispersed by the excitation-side light-dispersing device 2 into a spectrum of light, from which only a monochromatic light having a desired wavelength $\lambda_{Ex}$ is cast into the sample cell 3. By this light of wavelength $\lambda_{Ex}$, the sample contained in the sample cell 3 becomes excited and emits fluorescence. The emission-side light-dispersing device 4 and the detector 5 are provided for detecting the fluorescence emitted from the sample. The wavelength selected by the emission-side light-dispersing device 4 is adjusted at the fluorescence wavelength $\lambda_{Em}$. Since the fluorescence emitted from the sample is fainter than the light transmitted through the sample cell 3, the emission-side light-dispersing device 4 is located off the path of the irradiation light so that the transmitted light will not fall onto it. The detection result obtained with the detector 5 is fed to an output unit 6 and processed into a graph or the like.

Each of the excitation-side and emission-side light-dispersing devices 2 and 4 has a diffraction grating 21 or 41 and a grating drive mechanism 22 or 42. The set wavelengths of the excitation-side and emission-side light-dispersing devices 2 and 4 can be adjusted at desired wavelengths by directing the inclinations of the diffraction gratings 21 and 41 at predetermined angles by means of the grating drive mechanisms 22 and 42. Since the wavelength $\lambda_{Em}$ of the fluorescence is normally different from the wavelength $\lambda_{Ex}$ of the excitation light, different wavelengths are respectively set for the excitation-side and emission-side light-dispersing devices 2 and 4.

Patent Document 1: JP-A 2008-86562

DISCLOSURE OF THE INVENTION

Problem to be Solved by the Invention

In a sample analysis using a fluorescence spectrophotometer, it is necessary to set the optimal excitation wavelength and the optimal fluorescence wavelength for the sample to be analyzed. However for an unknown sample, it is difficult to set an optimal excitation wavelength and an optimal fluorescence wavelength.

It is generally known that, in many cases, an absorption wavelength of a sample is suitable as an excitation wavelength for that sample. The present invention has been developed with the aim of solving the aforementioned problem by using this knowledge. Its objective is to provide a fluorescence spectrophotometer applicable to a sample whose excitation wavelength or another analysis parameter is unknown.

Means for Solving the Problems

A fluorescence spectrophotometer according to the first mode of the present invention aimed at solving the aforementioned problem includes: a light source; a sample cell; an excitation-side light-dispersing system for dispersing a light from the light source and for casting a desired wavelength of light into the sample cell; an emission-side light-dispersing system for dispersing a light emitted from the sample cell, the emission-side light-dispersing system being located off an optical path of a transmitted light exiting from the sample cell after being cast from the excitation-side light-dispersing system into the sample cell; and a photodetector capable of detecting, among the light from the emission-side light-dispersing system, an emission light having the same wavelength as the light cast from the excitation-side light-dispersing system into the sample cell.

The fluorescence spectrophotometer according to the second mode of the present invention aimed at solving the aforementioned problem is a variation of the fluorescence spectrophotometer according to the first mode of the present invention, which includes: a controller for continuously varying the set wavelength of the excitation-side light-dispersing system and the set wavelength of the emission-side light-dispersing system over a predetermined wavelength range while keeping the two wavelengths equal to each other; and a spectrum data acquirer for obtaining spectrum data from detection results obtained with the photodetector for each of the set wavelengths of the excitation-side light-dispersing system and the emission-side light-dispersing system.

A liquid chromatograph system according to the third mode of the present invention aimed at solving the aforementioned problem includes the fluorescence spectrophotometer according to the second mode of the present invention and a separation column, wherein a sample separated into components by the separation column is passed through the sample cell together with a mobile phase, and the spectrum data acquirer obtains data on a temporal change of a spectrum for each of the set wavelengths.

Effect of the Invention

In general, when irradiated with a specific wavelength of light, an electron in a substance transitions to an excited state, absorbing an amount of energy from the irradiation light. Absorption spectroscopy uses this principle, in which the amount of light absorbed by a sample (absorption strength) is measured to analyze the sample. In normal absorptiometers, unlike fluorescence spectrometers, the photodetector is arranged so as to measure the intensity of light which has passed through the sample cell. The intensity of the transmitted light measured by the detector is compared with that of the irradiation light, and the sample analysis is performed based on the absorbance calculated from the intensity of light which is decreased due to the passage through the sample.

In the fluorescence spectrophotometer according to the present invention, since the emission-side light-dispersing system is located off the optical path of the transmitted light exiting from the sample cell after being cast from the excitation-side light-dispersing system into the sample cell, the light which has passed through the sample cell does not enter the emission-side light-dispersing system. The emission-side light-dispersing system is set at the same wavelength as the excitation-side light dispersing system. Since the fluorescence wavelength is normally different from the excitation wavelength, the photodetector in the present invention cannot detect the fluorescence generated by excitation even when the set wavelengths of the light-dispersing devices are equal to the excitation wavelength. It is the scattered light (Rayleigh-scattered light) resulting from the impingement of the irradiation light on the sample that enters the emission-side light-dispersing system of the present invention.

If the sample has some absorption characteristics against an irradiation light, the Rayleigh-scattered light will be weakened similarly to the transmitted light. Accordingly, in the spectrophotometer according to the present invention, when the irradiation light has an excitation wavelength, the amount of Rayleigh-scattered light detected by the photodetector will decrease. Since the spectrophotometer according to the present invention performs the wavelength scan while keeping the set wavelength of the excitation-side light-dispersing system and that of the emission-side light-dispersing system equal to each other, the set wavelength of the light-dispersing devices at the moment of a decrease in the amount of light detected by the photodetector corresponds to an absorption wavelength of the sample. Thus, the absorption characteristics of an unknown sample can be determined.

As noted earlier, the present invention uses the knowledge that, in many cases, an absorption wavelength of a sample is suitable as an excitation wavelength for that sample. Accordingly, once the absorption characteristics of an unknown sample are determined by the present invention, it is possible to deduce an appropriate excitation wavelength.

Incorporating the fluorescence spectrophotometer according to the present invention into a liquid chromatograph system provides a system capable of measuring a temporal change in the absorption-wavelength characteristics.

EXPLANATION OF NUMERALS

1 . . . Light Source
2 . . . Excitation-Side Light-Dispersing Device
3 . . . Sample Cell
4 . . . Emission-Side Light-Dispersing Device
5 . . . Detector
6 . . . Output Unit
7 . . . Controller
8 . . . Liquid Chromatograph System
11 . . . Flow Cell
21 . . . Excitation-Side Diffraction Grating
22 . . . Excitation-Side Grating Drive Mechanism
41 . . . Emission-Side Diffraction Grating
42 . . . Emission-Side Grating Drive Mechanism
81 . . . Separation Column
82 . . . Liquid-Supply Device

BEST MODE FOR CARRYING OUT THE INVENTION

Modes for carrying out the present invention are hereinafter described by means of FIGS. 2-6.

First Embodiment

Figure 1:
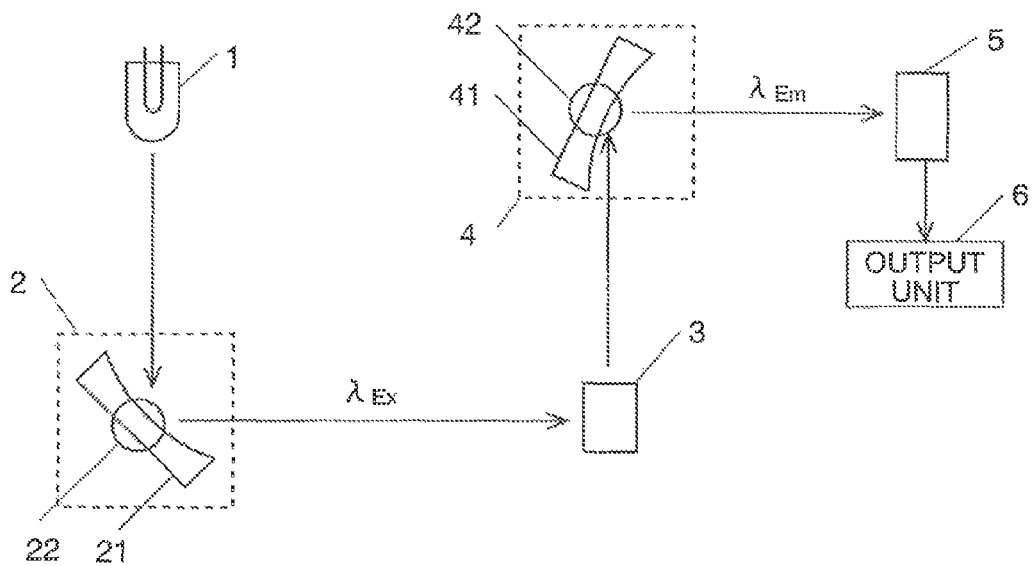
FIG. 1 is a schematic configuration diagram of a conventional fluorescence spectrophotometer.
Figure 2:
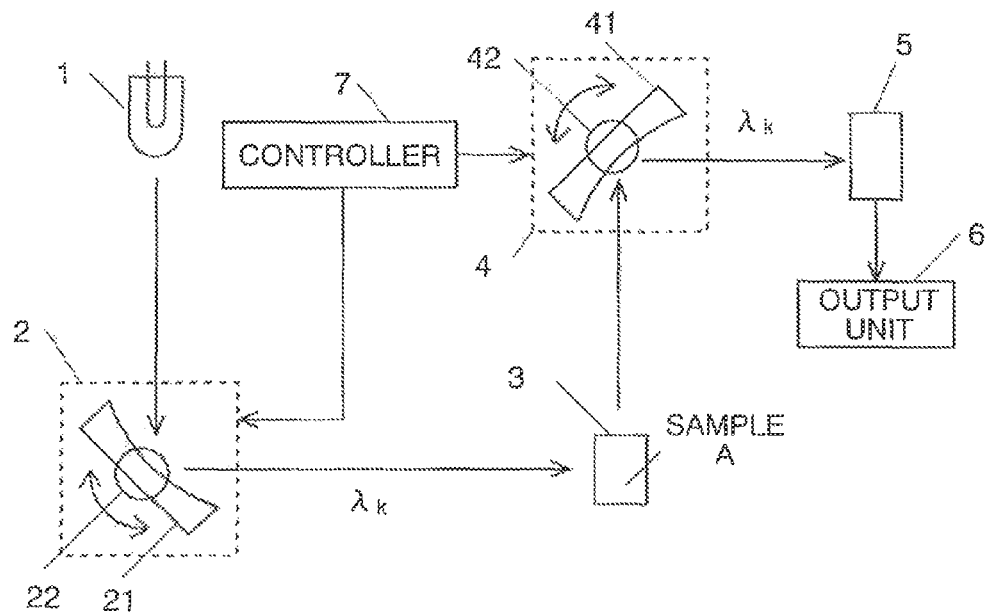
FIG. 2 is a schematic configuration diagram of a fluorescence spectrophotometer according to the first embodiment of the present invention.

FIG. 2 is a diagram showing a schematic configuration of a fluorescence spectrophotometer according to the first embodiment of the present invention. The same parts as used in the conventional fluorescence spectrophotometer (see FIG. 1) are denoted by the same numerals and will not be specifically described.

The configuration of the fluorescence spectrophotometer according to the present embodiment is basically the same as the conventional fluorescence spectrophotometer. A difference exists in that, under the control of a controller 7, the rotation angle of the excitation-side grating drive mechanism 22 and that of the emission-side grating drive mechanism 42 can be interlocked so as to perform a continuous wavelength scan while keeping the two wavelengths equal to the scan wavelength $\lambda_k$. The following description deals with the case of scanning a wavelength range from $\lambda_1$ to $\lambda_m$ so as to measure absorption characteristics over that wavelength range.

The controller 7 operates the grating drive mechanisms 22 and 42 to set the angles of the diffraction gratings 21 and 41 so that the set wavelengths of both the excitation-side light-dispersing device 2 and the emission-side light-dispersing device 4 will be $\lambda_1$. After a sample "A" having an unknown excitation wavelength is put in the sample cell 3, the light source 1 is energized, whereupon an excitation light of wavelength $\lambda_1$ is cast into sample A. Rays of light reflected by sample A fall onto the emission-side light-dispersing device 4, and only a Rayleigh-scattered light of wavelength $\lambda_1$ is detected by the detector 5. In this operation mode, the amplification factor of the detector 5 is set at a low level, since the scattered light is stronger than the fluorescence.

The controller 7 operates the grating drive mechanisms 22 and 42 in an interlocked fashion to gradually change the angles of the diffraction gratings 21 and 41 in small steps of $\Delta\theta$ until the set wavelength reaches $\lambda_m$. The detector 5 sends detection results for each wavelength to the output unit 6, which presents the absorption characteristics of sample A.

Figure 3:
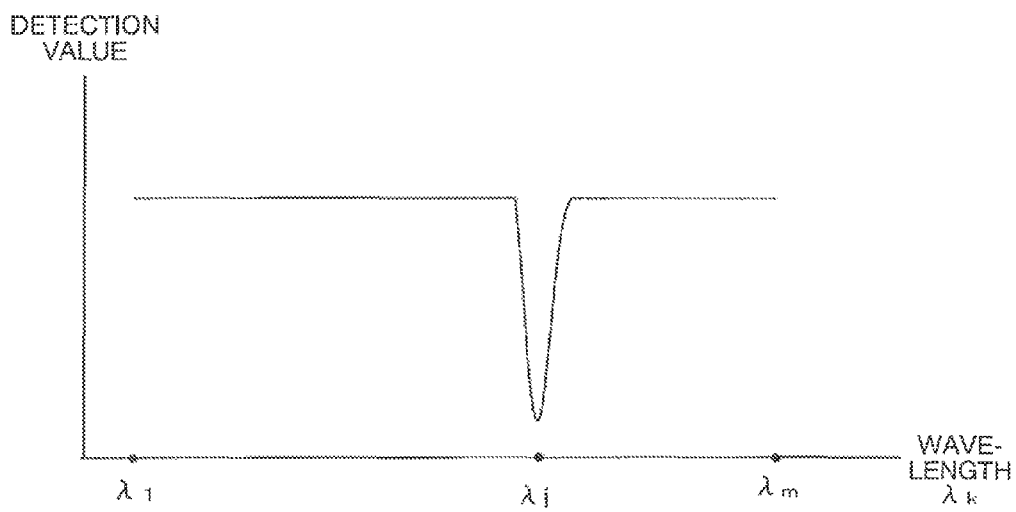
FIG. 3 is a spectral chart produced by the fluorescence spectrophotometer according to the first embodiment of the present invention.

FIG. 3 shows one example of the absorption characteristics of a sample presented by the output unit 6 of the first embodiment. The graph demonstrates that the Rayleigh-scattered light weakened when a light of wavelength $\lambda_i$ was cast. From this result, it can be expected that the light of wavelength $\lambda_i$ will cause an excitation of sample A, thus allowing various analyses on sample A, such as identification of the sample or a fluorescence measurement on the sample. Since the vertical axis in FIG. 3 indicates the detection values obtained with the detector 5, the peak at the absorption wavelength $\lambda_i$ has a negative value. It is also possible to obtain a positive peak, as in the case of a chromatogram of a commonly used fluorescence spectrophotometer or absorption spectrophotometer, by inverting the polarity of the detection values by the output unit 6.

Second Embodiment

Figure 4:
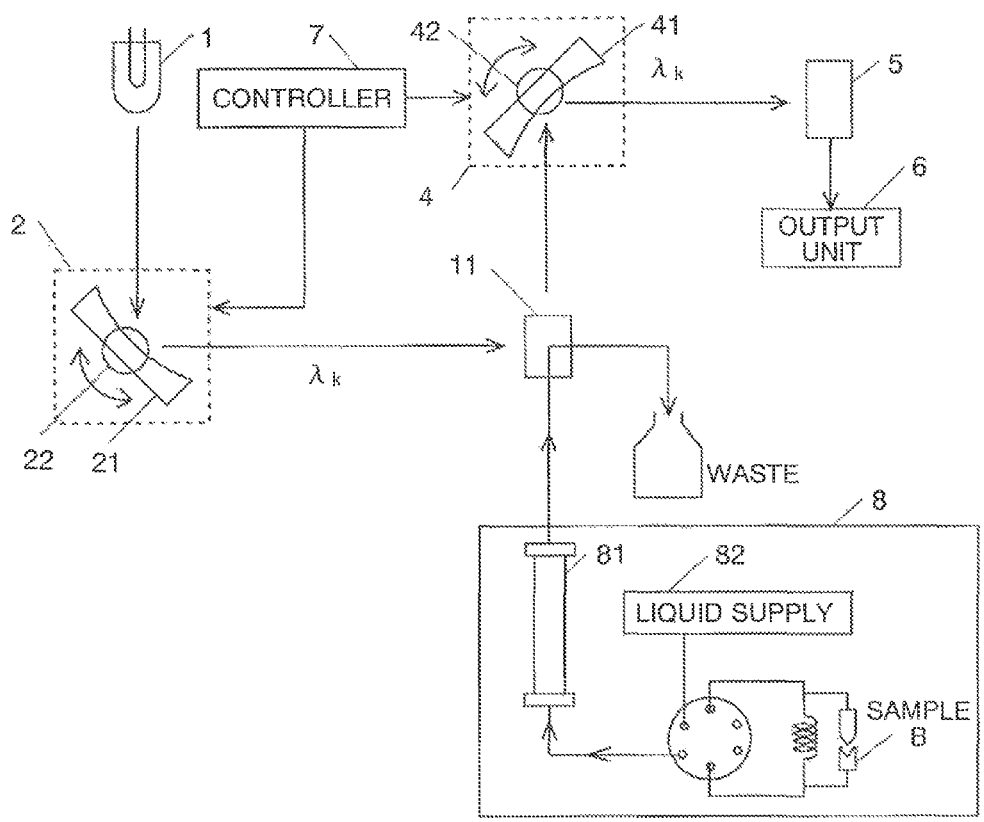
FIG. 4 is a schematic configuration diagram of a liquid chromatograph system using a fluorescence spectrophotometer according to the second embodiment of the present invention.

FIG. 4 is a diagram showing a schematic configuration of a liquid chromatograph system using a fluorescence spectrophotometer according to the second embodiment of the present invention. The same parts as used in the spectrophotometer of the first embodiment (see FIG. 2) are denoted by the same numerals and will not be specifically described.

The configuration of the fluorescence spectrophotometer according to the present embodiment is basically the same as the spectrophotometer of the first embodiment. A difference exists in that a flow cell 11 is used in place of the sample cell 3. A passage extending from a separation column 81 of the liquid chromatograph 8 is connected to the flow cell 11. Similar to the first embodiment, the following description deals with the case of scanning a wavelength range from $\lambda_1$ to $\lambda_m$ so as to measure absorption characteristics over that wavelength range for each of the components of sample "B" separated by and sequentially introduced from the separation column 81.

The liquid-supply device 82 supplies a mobile phase, which carries sample B into the separation column 81. While passing through the separation column 81, the sample is temporally separated into components, which are eluted from the column to be sequentially introduced into the flow cell 11. The controller 7 conducts a wavelength scan over a wavelength range from $\lambda_1$ to $\lambda_m$, while interlocking the operations of the excitation-side light-dispersing device 2 and the emission-side light-dispersing device 4 so as to keep the set wavelengths of these devices equal to each other. Since the components separated from sample B in the separation column 81 are sequentially introduced into the flow cell 11, the wavelength scan is repeated until sample B is completely eluted. The detector 5 produces a detection signal showing the result of each wavelength scan of the sequentially introduced sample B and feeds it to the output unit 6. The output unit 6 creates a three-dimensional chromatogram showing a temporal change in the absorption characteristics of sample B with the three axes of signal intensity A, wavelength $\lambda_k$ and time T.

Figure 5:
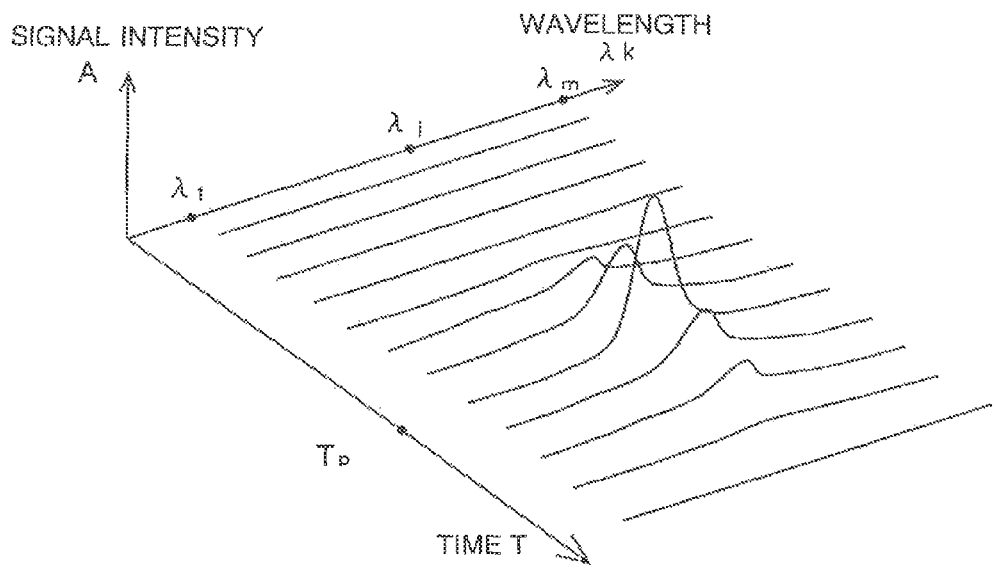
FIG. 5 is a three-dimensional spectral chart produced by the fluorescence spectrophotometer according to the second embodiment of the present invention.

FIG. 5 is one example of the three-dimensional chromatogram created by the output unit 6. In this example, the polarity of the detection values obtained with the detector 5 is inverted so that the signal intensity at the point of absorption is represented as a positive peak, similar to a chromatograph obtained with a commonly used fluorescence spectrophotometer or absorption spectrophotometer. This chromatograph demonstrates that component b in sample B is eluted at Tp seconds from the beginning of the detection process and absorbs light at wavelength $\lambda_j$. That is to say, the excitation wavelength for component b contained in sample B is $\lambda_j$.

The previous embodiments 1 and 2 took the example of performing a wavelength scan for a sample whose excitation wavelength and absorption wavelength are unknown. For a sample whose excitation wavelength and absorption wavelength are known, the spectrophotometer according to the present invention can be used like an absorptiometer to perform a quantitative analysis or the like of the sample. In that case, it should be noted that what is detected is not the light transmitted through the sample but the Rayleigh-scattered light produced by the sample.

With the fluorescence spectrophotometer according to the present invention, both the fluorescence detection and the absorbance measurement can be performed by merely changing the wavelength setting of the emission-side light-dispersing device. The present invention effectively allows the same spectrophotometer to be used for both an analysis of a substance that does not emit fluorescence (e.g. caffeine) and an analysis of a normal substance that emits fluorescence due to excitation.

Figure 6:
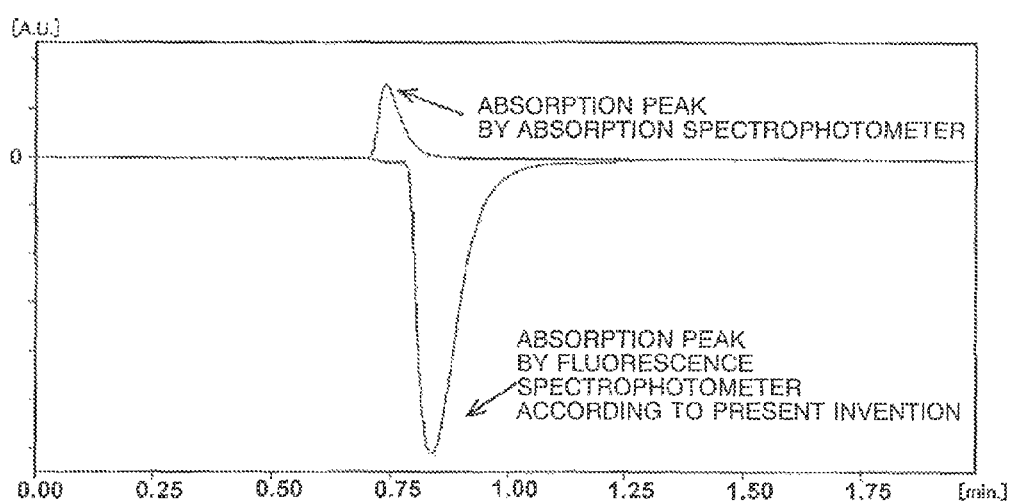
FIG. 6 is a chart showing spectra of caffeine obtained with the fluorescence spectrophotometer according to the second embodiment of the present invention and a commonly used absorption spectrophotometer.

FIG. 6 shows the detection values (the lower peak in FIG. 6) observed when a caffeine-containing sample was introduced from a separation column of a liquid chromatograph into the flow cell 11 of the fluorescence spectrophotometer according to the second embodiment of the present invention, superimposed on the signal intensities (the upper peak in FIG. 6) observed when the same caffeine-containing sample was introduced into the flow cell of as normal absorption spectrophotometer. In both measurements, the absorption wavelength (the set wavelength of the light-dispersing device used for casting light into the sample cell) was set at 272 nm. The measurement conditions were the same.

In the case of the normal absorption spectrophotometer, since the detector is located on the extended line of the path of the excitation light, it is the light transmitted through the sample cell that is detected by the detector. Accordingly, an absorbance peak appears at the point in time where caffeine passes through the flow cell. In the case of the fluorescence spectrophotometer according to the second embodiment of the present invention, the Rayleigh-scattered light is detected instead of the transmitted light. The experiment showed that the Rayleigh-scattered light weakened at the point in time where caffeine passed through the flow cell. These results demonstrate that the fluorescence spectrophotometer according to the present invention can be used like an absorption spectrophotometer.

It should be noted that the present invention is not limited to the previously described embodiments but can be changed within the spirit and scope of the present invention.

The invention claimed is:

1. A fluorescence spectrophotometer, comprising:
a light source;
a sample cell;
an excitation-side light-dispersing system for dispersing a light from the light source and for casting a desired wavelength of light into the sample cell;
an emission-side light-dispersing system for dispersing a light emitted from the sample cell, the emission-side light-dispersing system being located off an optical path of a transmitted light exiting from the sample cell after being cast from the excitation-side light-dispersing system into the sample cell;
a photodetector capable of detecting, among the light from the emission-side light-dispersing system, an emission light having a same wavelength as the light cast from the excitation-side light-dispersing system into the sample cell;
a controller for continuously varying a set wavelength of the excitation-side light-dispersing system and a set wavelength of the emission-side light-dispersing system over a predetermined wavelength range while keeping the two wavelengths equal to each other; and
a spectrum data acquirer for obtaining spectrum data from detection results obtained with the photodetector for each of the set wavelengths of the excitation-side light-dispersing system and the emission-side light-dispersing system.

2. A liquid chromatograph system, comprising a fluorescence spectrophotometer and a separation column, the fluorescence spectrophotometer including:
a light source;
a sample cell;
an excitation-side light-dispersing system for dispersing a light from the light source and for casting a desired wavelength of light into the sample cell;
an emission-side light-dispersing system for dispersing a light emitted from the sample cell, the emission-side light-dispersing system being located off an optical path of a transmitted light exiting from the sample cell after being cast from the excitation-side light-dispersing system into the sample cell;

a photodetector capable of detecting, among the light from the emission-side light-dispersing system, an emission light having a same wavelength as the light cast from the excitation-side light-dispersing system into the sample cell;

a controller for continuously varying a set wavelength of the excitation-side light-dispersing system and a set wavelength of the emission-side light-dispersing system over a predetermined wavelength range while keeping the two wavelengths equal to each other; and a spectrum data acquirer for obtaining spectrum data from detection results obtained with the photodetector for each of the set wavelengths of the excitation-side light-dispersing system and the emission-side light-dispersing system, wherein:

a sample separated into components by the separation column is passed through the sample cell together with a mobile phase; and the spectrum data acquirer obtains data on a temporal change of a spectrum for each of the set wavelengths.

3. A method for detecting an excitation wavelength in a fluorescence spectrophotometer having:

a light source;

a sample cell;

an excitation-side light-dispersing system for dispersing a light from the light source and for casting a desired wavelength of light into the sample cell;

an emission-side light-dispersing system for dispersing a light emitted from the sample cell, the emission-side light-dispersing system being located off an optical path of a transmitted light exiting from the sample cell after being cast from the excitation-side light-dispersing system into the sample cell; and a photodetector capable of detecting, among the light from the emission-side light-dispersing system, an emission light having a same wavelength as the light cast from the excitation-side light-dispersing system into the sample cell, the method comprising steps of:

continuously varying a set wavelength of the excitation-side light-dispersing system and a set wavelength of the emission-side light-dispersing system over a predetermined wavelength range while keeping the two wavelengths equal to each other;

obtaining spectrum data from detection results obtained with the photodetector for each of the set wavelengths of the excitation-side light-dispersing system and the emission-side light-dispersing system; and detecting an excitation wavelength of a sample from the obtained spectrum data.

* * * * *